United States Patent [19]

Hanifl

[11] Patent Number: 4,834,715
[45] Date of Patent: May 30, 1989

[54] NEEDLE ANTI-RESHEATHER

[75] Inventor: Paul H. Hanifl, Barrington, Ill.

[73] Assignee: Sage Products, Inc., Cary, Ill.

[21] Appl. No.: 236,266

[22] Filed: Aug. 24, 1988

Related U.S. Application Data

[63] Continuation of Ser. No. 91,053, Aug. 28, 1987, abandoned.

[51] Int. Cl.⁴ .............................................. A61M 5/32
[52] U.S. Cl. .................................... 604/192; 604/263
[58] Field of Search ................ 604/192, 187, 198, 263

[56]  References Cited

U.S. PATENT DOCUMENTS

| | | | |
|---|---|---|---|
| 3,485,239 | 12/1969 | Vanderbeck | 604/192 |
| 4,220,151 | 9/1980 | Whitney | 604/110 |
| 4,300,678 | 11/1981 | Gyure et al. | 604/192 |
| 4,475,903 | 10/1984 | Steenhuisen et al. | 604/111 |

Primary Examiner—John D. Yasko
Attorney, Agent, or Firm—Lee & Smith

[57]  ABSTRACT

An anti-resheathing device for preventing a needle sheath from re-engaging the hub of a needle after the sheath has been disengaged from the hub when the needle hub has been inserted in a needle retention socket. The sheath has a pre-determined exterior dimension in that portion of the sheath adjacent the needle retention socket. A wall extends outwardly from the socket toward the sheath, and has an interior dimension less than the exterior dimension of the sheath and is constructed of a displaceable material having a memory such that the wall is displaced to accommodate the sheath when the hub is inserted within the socket. When the sheath is then removed from the hub, the wall returns to a substantially undisplaced orientation and, due to the exterior dimension of the wall, prevents the sheath from being re-engaged on the hub.

9 Claims, 1 Drawing Sheet

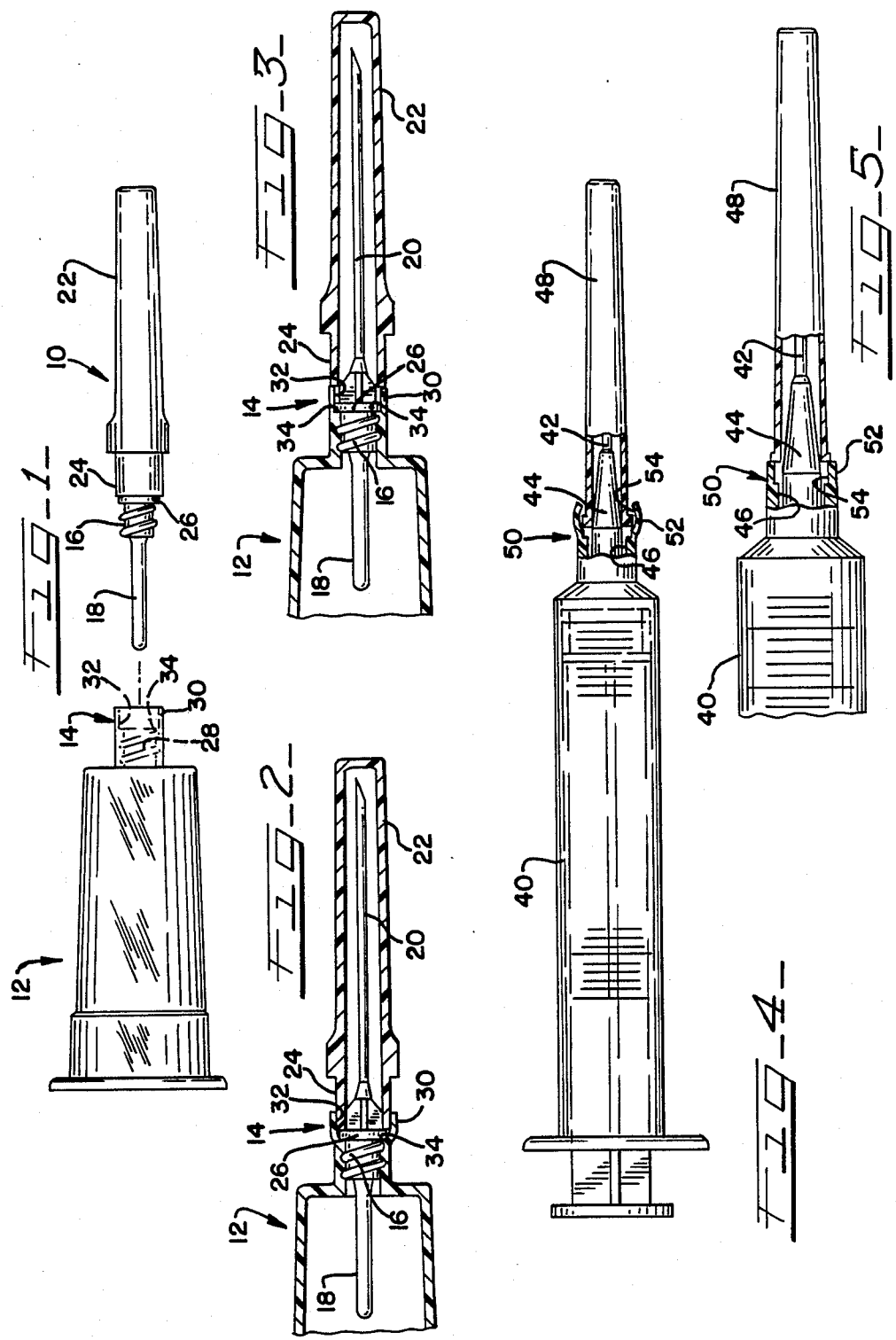

NEEDLE ANTI-RESHEATHER

This application is a continuation of application Ser. No. 91,053, filed Aug. 28, 1987 now abandoned.

BACKGROUND OF THE INVENTION

This invention relates to sheathing of needles such as those used for blood work and injections, and relates particularly to a device for preventing resheathing of a needle after the hub of the needle has been inserted in a needle retention socket and the sheath then disengaged from the hub.

For cleanliness purposes and in order to avoid any possibility of contamination, needles for use with humans are designed for a single use and then disposal. A typical needle is sheathed before use with the sheath being discarded after being removed from the needle. Normally, the sheath is formed such that it is retained on the hub of the needle, that portion of the needle that may be installed within a needle retention socket of a needle receiving implement, such as a blood needle holder or a syringe.

Often, a nurse or doctor will resheath a needle after its use, and if great care is not exercised, the resheathed needle can inadvertently become intermixed with unused needles and possibly be reused. Were the sheath incapable of being replaced on the needle, such confusion would be far less likely.

SUMMARY OF THE INVENTION

The invention provides an anti-resheathing device for preventing a needle sheath from being re-engaged on the hub of a needle after the sheath has been disengaged from the hub and after the needle hub has been inserted in a needle retention socket such as that of a blood needle hub or a syringe. The sheath has a predetermined exterior dimension in that portion of the sheath that is adjacent to the socket. A wall extends from the socket in the direction of the sheath, the wall having an interior dimension less than the exterior dimension of the sheath and the wall being constructed of a displaceable material having a memory such that the wall may be displaced to accommodate the sheath when the hub is inserted within the socket. When the sheath is then disengaged from the hub, the wall returns to a substantially undisplaced orientation. Since the interior dimension of the wall is less than the exterior dimension of the sheath, the wall thus prevents the sheath from being re-engaged upon the needle hub.

In accordance with the disclosed embodiment of the invention, the sheath is cylindrical, and the extending wall is likewise cylindrical and is formed of a plastic material capable of stretching in order to be displaced to accommodate the sheath. Other forms of the wall, such as a partial cylinder or fingers extending from the socket may be used in place of the full cylindrical wall so long as the interior dimension of the wall is less than the exterior dimension of the sheath.

A seat for the hub is formed within the socket, and the wall extends from the seat. The seat comprises a cylindrical ledge against which the hub rests when installed within the socket.

In the normal needle installation, a portion of the hub normally protrudes from the socket. The wall of the anti-resheather according to the invention is formed extending over the protruding part. Preferably, the wall extends over substantially all of the protruding part.

BRIEF DESCRIPTION OF THE DRAWING

The invention is described in the following description of preferred embodiments of the invention, taken in conjunction with the drawing figures in which:

FIG. 1 illustrates a sheathed blood needle in engagement alignment with a blood needle holder having an anti-resheathing device according to the invention, FIG. 2 is an enlarged cross-sectional view of the blood needle and the blood needle holder of FIG. 1 after the blood needle has been installed within the blood needle holder but before the sheath has been removed, FIG. 3 is a cross sectional view similar to FIG. 2 but illustrating the inability of the sheath to be re-engaged upon the needle hub after having been removed, FIG. 4 illustrates the anti-resheathing device according to the invention when employed as a part of a syringe, with portions broken away to illustrate detail, and FIG. 5 is an enlarged fragmentary view of the embodiment of FIG. 4, illustrating prevention of re-engagement of the sheath upon the needle hub after having once been removed.

DESCRIPTION OF THE PREFERRED EMBODIMENTS

A first embodiment of the invention is illustrated in FIGS. 1 through 3. In this form of the invention, a conventional blood needle 10 is shown in alignment with and subsequent engagement with a blood needle holder 12 including an anti-resheather 14 according to the invention. The blood needle 10 is comprised of a hub 16 and oppositely extending needles 18 and 20, the needle 18 being housed within a flexible protective cover which may be displaced to expose the needle in a conventional fashion. A sheath 22 is installed on the hub 16 to prevent contact with the needle 20. The sheath 22 has a cylindrical end 24 which butts against an integral stop 26 forming part of the hub 16. Normally, the blood needle 10 is provided with a second sheath (not illustrated) which is engaged over the needle 18 onto the cylindrical end 24 of the sheath 22, but which is discarded before the blood needle 10 is installed in the holder 12.

The holder 12 may be of a conventional design having an internal thread 28 forming a socket for reception of the hub 16. The anti-resheather 14 of the invention is formed on the blood needle holder 12, extending outwardly from the threaded socket 28, and comprises a wall 30 having a cylindrical inner surface 32. The wall 30 extends from a seat 34 formed at the mouth of the internally threaded socket 28.

The wall 30 is formed of a displaceable material, such as plastic, which has a memory and which is capable of being stretched in order to accommodate the cylindrical end 24 of the sheath 22. As best illustrated in FIG. 3, the inner diameter of the sheath 30 at the inner surface 32 is less than the outer diameter of the cylindrical end 24 of the sheath 22.

When properly installed within the blood needle holder 12, the hub 16 of the blood needle 10 protrudes from the internally threaded socket 28. The wall 30 is formed to extend over that protruding part, and preferably extends over substantially all of the protruding part, so that re-engagement of the sheath 22, once disengaged from the hub 16, is prevented.

The anti-resheathing feature of the invention is employed as follows. The blood needle 10 is installed within the blood needle holder 12 by engaging the hub 16 within the internally threaded socket 28. The sheath 22 remains engaged on the hub 16 during this procedure. As the blood needle 10 is installed, the sheath 22, which has the larger diameter cylindrical end 24, stretches and is engaged beneath the wall 30, in contact with the inner surface 32. The integral stop 26 is located against the seat 34 when the blood needle 10 is fully installed within the blood needle 12.

When the blood needle 10 is then used, the sheath 22 is withdrawn to expose the needle 20. Removal of the sheath 22 permits the stretched wall 30 to relax and return to a substantially unstretched orientation. If one were to attempt to resheath the needle 20 with the sheath 22, as illustrated in FIG. 3, because of the relative dimensioning of the wall 30 and the cylindrical end 24, the end 24 butts the wall 30, and cannot be re-engaged upon the hub 16 without considerable force.

A second form of the invention is illustrated in FIGS. 4 and 5. A conventional syringe 40 includes, as is typical, a needle 42 mounted within a hub 44 which has been inserted within a socket 46 in the syringe 40, typically by being threaded thereinto. A sheath 48 is installed on the hub 44 over the needle 42 to prevent premature contact with the needle 42 and its contamination.

The syringe 40 is formed with an integral anti-resheather 50 which is essentially identical to the anti-resheather 14 of the embodiment of FIGS. 1 through 3. The anti-resheather 50 includes a wall portion 52 having an inner surface 54 in contact with one end of the sheath 48. Preferably, and in the same fashion as the anti-resheather 14 discussed above, the anti-resheather 50 is formed of a plastic material having a memory and which is capable of stretching in order to be displaced. When the sheath 48 is removed, the material of the anti-resheather 50 relaxes to a substantially undisplaced orientation, as shown in FIG. 5.

As best illustrated in FIG. 5, the interior dimension of the wall 52 at the inner surface 54 is less than the exterior dimension of the adjacent portion of the sheath 48. This assures that once the sheath 48 is removed from the hub 40, its replacement will be extremely difficult, if not impossible. As shown, attempted replacement of the sheath 48 causes the end of the sheath 48 to butt the anti-resheather 50, preventing re-engagement.

The syringe 40 is typically provided in an assembled fashion with the needle 42 and sheath 48 in place. Removal of the sheath 48 permits the temporarily stretched wall 52 to relax to essentially the orientation illustrated in FIG. 5, preventing resheathing. The sheath 48 can be initially installed beneath the extended wall 52 in one of many different manners. For example, before threading of the hub 44 into the socket 46, the sheath 48 can be mounted on the hub 44 and the combination of the sheath 48 and hub 44 then threaded into the hub 46. During the threading procedure, the semi-flexible nature of the anti-resheather 50 permits the wall 52 to be stretched in order to accommodate the end of the sheath 48. Once the sheath 48 is withdrawn from the hub 44, however, its replacement is extremely difficult because the mechanical advantage of its rotational insertion is no longer available since the hub 44 remains in place.

The invention provides a simple, yet highly effective means of preventing resheathing of a needle installed within a needle retention socket once the sheath has been removed. Various changes can be made to the invention without departing from the spirit thereof or scope of the following claims.

What is claimed is:

1. An anti-resheathing device for preventing a needle sheath from reengaging the hub of a needle after the sheath has been disengaged from the hub and after the needle hub has been inserted in a needle retention socket, the sheath having a predetermined exterior dimension in that portion of the sheath adjacent the socket, comprising a wall extending from said socket toward said sheath, said wall having an interior dimension less than the exterior dimension of the sheath, and said wall being constructed of a displaceable material having a memory such that said wall may be displaced to accommodate said sheath when said hub is inserted within said socket and said wall returns to a substantially undisplaced orientation when said sheath is disengaged from said hub.

2. An anti-resheathing device according to claim 1 in which said sheath portion is cylindrical.

3. An anti-resheathing device according to claim 1 in which said wall is cylindrical and is formed of a plastic material capable of stretching in order to be displaced to accommodate said sheath.

4. An anti-resheathing device according to claim 1 including a seat for said hub formed within said socket, said wall extending from said seat.

5. An anti-resheathing device according to claim 4 in which said seat comprises a cylindrical ledge.

6. An anti-sheathing device according to claim 1 in which said hub has a part protruding from said socket, said wall extending over said protruding part.

7. An anti-resheathing device according to claim 6 in which said wall extends over substantially all of said protruding part.

8. A method of preventing resheathing of a needle after the needle has been inserted in a needle retention socket and the sheath removed, the needle having a hub engageable in the socket and the sheath having a predetermined exterior dimension in that portion of the sheath adjacent the socket when the needle is installed in the socket, the method comprising the steps of a. forming a wall extending from the socket, the wall being of a displaceable material having a memory and having an interior dimension less than the exterior dimension of the sheath, b. installing said needle, when sheathed, into said socket by inserting the hub within the socket, the sheath extending beneath and displacing the wall outwardly, c. removing the sheath and permitting the wall to return to a substantially undisplaced orientation.

9. A method according to claim 8 in which method step "a" includes forming said wall in a cylindrical fashion of a plastic material capable of being temporarily stretched during method step "b".

* * * * *